US 6,620,904 B2

(12) United States Patent
Lemke

(10) Patent No.: US 6,620,904 B2
(45) Date of Patent: Sep. 16, 2003

(54) PROCESSES FOR PREPARING LINEAR POLYGLYCEROLS AND POLYGLYCEROL ESTERS

(75) Inventor: Daniel Wayne Lemke, Cokato, MN (US)

(73) Assignee: Lonza Inc., Fair Lawn, NJ (US)

(*) Notice: Subject to any disclaimer, the term of this patent is extended or adjusted under 35 U.S.C. 154(b) by 8 days.

(21) Appl. No.: 10/012,026

(22) Filed: Nov. 6, 2001

(65) Prior Publication Data

US 2002/0058781 A1 May 16, 2002

Related U.S. Application Data

(60) Provisional application No. 60/246,202, filed on Nov. 6, 2000.

(51) Int. Cl.[7] .............................................. C08G 63/48
(52) U.S. Cl. .................... 528/295.5; 528/275; 528/300; 528/301; 524/788
(58) Field of Search ................. 528/275, 300, 528/301, 295.5; 524/788

(56) References Cited

U.S. PATENT DOCUMENTS

| 2,258,892 A | * | 10/1941 | Harris .......................... 568/679 |
| 3,637,774 A | * | 1/1972 | Babayan et al. ............. 521/172 |
| 3,968,169 A | * | 7/1976 | Seiden et al. ................ 568/680 |
| 4,960,953 A | * | 10/1990 | Jakobson et al. ............ 568/621 |
| 5,243,086 A | * | 9/1993 | Jakobson et al. ............ 568/619 |
| 2002/0058781 A1 | * | 5/2002 | Lemke ........................ 528/425 |

FOREIGN PATENT DOCUMENTS

| EP | 0505002 | 3/1992 |
| EP | 0333984 | 7/1993 |
| JP | 61238749 | 10/1986 |
| JP | 1125338 | 5/1989 |
| JP | 2172938 | 7/1990 |
| JP | 6279342 | 10/1994 |
| WO | 95/16723 | * 6/1995 |

* cited by examiner

Primary Examiner—Samuel A. Acquah
(74) Attorney, Agent, or Firm—Darby & Darby

(57) ABSTRACT

Applicant has discovered processes for preparing polyglycerols and polyglycerol esters in high yield and with minimal formation of cyclic polyglycerols and cyclic polyglycerol esters. Furthermore, the processes of this invention produce a high proportion of linear polyglycerols and polyglycerol esters. The linear polyglycerols have very desirable physical characteristics, including a clear appearance at melt, a desirable Gardner color, a mild odor, and a bland taste. The polyglycerols and polyglycerol esters prepared by the method of the present invention are well suited for use as cosmetic and food additives. Since few, if any, cyclic polyglycerols and polyglycerol esters are formed by the processes of this invention, costly and time consuming distillation steps to remove such by-products are not needed. More specifically, applicants have discovered that if a calcium containing compound, such as calcium hydroxide, is used in place of potassium or sodium hydroxide during polymerization of glycerol, polyglycerol, or a mixture thereof or esterification of polyglycerols, the formation of cyclic polyglycerols is greatly reduced. One embodiment of the invention is a method of preparing a polyglycerol comprising polymerizing glycerol, polyglycerol, or a mixture thereof in the presence of a calcium containing compound, such as calcium hydroxide. Preferably, the calcium containing compound is present in a catalytically effective amount. Another embodiment is a method of preparing a polyglycerol ester by esterifying a polyglycerol in the presence of a calcium containing compound.

39 Claims, No Drawings

PROCESSES FOR PREPARING LINEAR POLYGLYCEROLS AND POLYGLYCEROL ESTERS

This application claims the benefit of U.S. Provisional Application No. 60/246,202, filed Nov. 6, 2000, which is hereby incorporated by reference.

FIELD OF THE INVENTION

The present invention relates to methods for preparing polyglycerols and polyglycerol esters, while minimizing formation of cyclic polyglycerols and polyglycerol esters.

BACKGROUND OF THE INVENTION

Polyglycerols and polyglycerol esters are well known in the art. They are commercially available as food, cosmetic, and pharmaceutical emulsifiers, and frequently used as textile lubricants, plastic anti-static agents, defoamers, anti-bloom agents for edible coatings, and anti-splattering agents in cooking oil.

Polyglycerols are commonly prepared by mixing glycerol with an alkali metal catalyst, such as sodium or potassium hydroxide, and then heating the mixture to an elevated temperature. This reaction causes the condensation or dehydration of two glycerol molecules α-hydroxyl groups resulting in an ether bond between the glycerol molecules and the release of water. The unreacted α-hydroxy groups remain available to react with the hydroxy groups of additional glycerol molecules and/or other polymerized molecules.

This method produces a mixture of linear, branched, and cyclic polyglycerols. Cyclic polyglycerols, however, often cause degradation of products into which they are incorporated, detrimentally affecting the taste, performance, and odor of the products. Therefore, there have been continuing efforts to find a method of preparing linear polyglycerols which produce little, if any, cyclic polyglycerols. Cyclic polyglycerols generally have significantly lower hydrophilic-lipophilic (HLB's) than similar linear polyglycerols. As a result, they typically act as emulsion breakers rather than emulsion builders. Also, the presence of cyclic polyglycerols and cyclic polyglycerol esters promotes free polyglycerol in high mono ester products to precipitate out of solution to produce a two phase system. This makes high mono ester products difficult if not impossible to manufacture on a commercial basis. Polyglycerol esters prepared with a low mole ratio of fatty acid to polyglycerol have a tendency not to be homogeneous at reaction temperature. The situation is worse when cyclic polyglycerols are brought into the system.

Harris, U.S. Pat. No. 2,258,892, describes a method for preparing polyglycerol ethers. The method comprises heating glycerol alone or in the presence of a catalyst to form polyglycerol and etherifying the polyglycerol with a particular alcohol, alkyl halide, alkyl sulphate, or mixture thereof to form a polyglycerol ether.

In U.S. Pat. No. 3,637,774, Babayan describes a process for preparing polyglycerols and esters thereof which have good color and little, if any, odor. The process involves the condensation of glycerol in the presence of an alkaline catalyst in an anhydrous medium at a temperature above 100° C. After the condensation has been completed, the reaction mixture is allowed to cool. It is then diluted with water and a bleaching agent is added. The temperature of the mixture is maintained below 100° C. for a time sufficient to bleach the product.

Many methods for enhancing the color, odor, and taste of polyglycerols and for reducing the concentration of cyclic polyglycerols in polyglycerol mixtures have been developed. For example, in the method described in Japanese Patent Publication No. 1125338, glycerol is condensed in the presence of an alkali catalyst and aluminum oxide or an aluminum oxide-based absorbent. Low-boiling point components, including unreacted glycerol, are then distilled off and the mixture condensed again to yield polyglycerols.

Japanese Patent Publication No. 61238749 discloses a method of preparing polyglycerols with low cyclic polyglycerol content. The method includes condensing glycerol in the presence of an alkali catalyst and an aluminum oxide absorbent.

Japanese Patent Publication No. 2172938 discloses a process for preparing polyglycerols having a low content of low molecular weight substances, including cyclic substances. The process involves condensation of glycerol in the presence of an alkaline catalyst at controlled temperature and pressure conditions.

Seiden et al., U.S. Pat. No. 3,968,169, disclose heating glycerol under reduced pressure in the presence of a catalytic amount of adjuvants capable of promoting the polymerization of glycerol to form polyglycerols. The condensation reaction is terminated by adding a neutralizing agent to the mixture. Unreacted glycerol and cyclic diglycerol are subsequently removed by distillation. The polyglycerol can optionally be esterified with a fatty acid to form a polyglycerol ester.

In Japanese Patent Publication No. 6279342, the content of cyclic polyglycerols in a crude polyglycerol mixture is reduced by first reacting the mixture with epichlorohydrin in the presence of a Lewis acid and then reacting it with an alkaline aqueous solution.

Jakobson et al., U.S. Pat. No. 4,960,953, disclose a process for preparing polyglycerols which are low in cyclic components. The process comprises reacting glycerol, diglycerol, or a high polyglycerol with epichlorohydrin at 90 to 170° C. to produce a crude chlorohydrin/ether mixture; adding an amount of a strong base at least substantially equivalent to the organically bound chlorine content of the chlorohydrin/ether mixture; and desalting the mixture and recovering the glycerol, diglycerol, and higher polyglycerol fractions.

Jakobson et al., U.S. Pat. No. 5,243,086, describe a process for the preparation of diglycerol and other polyglycerols substantially free of cyclic glycerol compounds. In this process, isopropylideneglycerol is reacted with α-monochlorohydrin in the presence of at least one alkaline compound to yield monoisopropylidenediglycerol. The reaction mixture containing monoisopropylidenediglycerol is reacted with water in the presence of at least one acidic catalyst to yield diglycerol and other polyglycerols and acetone.

International Patent Publication No. WO 95/16723 disclose polymerizing glycerol, 2,2-dimethyl-1,3-dioxolane-4-methanol, glycidol, or glycerol carbonate in the presence of an anionic clay to form a polymer of glycerol.

There is a continuing need for more cost effective and faster methods of preparing polyglycerols containing little, if any, cyclic polyglycerols.

SUMMARY OF THE INVENTION

Applicants have discovered processes for preparing polyglycerols and polyglycerol esters in high yield and with minimal formation of cyclic polyglycerols and cyclic polyglycerol esters. Furthermore, the processes of this invention produce a high proportion of linear polyglycerols and polyglycerol esters. The linear polyglycerols have very desirable physical characteristics, including a clear appearance at melt, a desirable Gardner color, a mild odor, and a bland taste. The polyglycerols and polyglycerol esters prepared by the method of the present invention are well suited for use as cosmetic and food additives. Since few, if any, cyclic polyglycerols and polyglycerol esters are formed by the processes of this invention, costly and time consuming distillation steps to remove such by-products are not required.

More specifically, applicants have discovered that if a calcium containing compound, such as calcium hydroxide, is used in place of potassium or sodium hydroxide during polymerization of glycerol or esterification of polyglycerols, the formation of cyclic polyglycerols is greatly reduced.

One embodiment of the invention is a method of preparing a polyglycerol comprising polymerizing glycerol, polyglycerol, or a mixture thereof in the presence of a calcium containing compound, such as calcium hydroxide. Preferably, the calcium containing compound is present in a catalytically effective amount. Typically, less than about 8% by weight of cyclic polyglycerols are formed, based upon 100% by weight of total polyglycerols.

Another embodiment is a method of preparing a polyglycerol ester by esterifying or transesterifying a polyglycerol in the presence of a calcium containing compound. According to a preferred embodiment, the polyglycerol is esterified by reacting it with a fatty acid or a triglyceride in the presence of a calcium containing compound.

DETAILED DESCRIPTION OF THE INVENTION

The present invention provides processes for preparing polyglycerols and polyglycerol esters. These processes produce linear polyglycerols and linear polyglycerol esters in high yield, while minimizing formation of cyclic polyglycerols and cyclic polyglycerol esters. Typically, less than about 8% and preferably less than about 5% by weight of cyclic polyglycerols and polyglycerol esters are formed by these processes (based upon 100% total weight of polyglycerols and polyglycerol esters). The polyglycerols and polyglycerol esters prepared by the processes of the present invention are suitable for use as cosmetic and food additives. Polyglycerol esters prepared by the process of the present invention are phase stable, low in odor and color, bland in taste, and relatively cheap to manufacture.

In any identified embodiments, the term "about" means within 50%, preferably within 25%, and more preferably within 10% of a given value or range. Alternatively, the term "about" means within an acceptable standard error of the mean, when considered by one of ordinary skill in the art.

The term "calcium containing compound" includes any salt containing a calcium cation, such as calcium hydroxide, calcium oxide, calcium carbonate, and mixtures thereof. A preferred calcium containing compound is calcium hydroxide.

The term "polyglycerol" as used herein includes, but is not limited to, diglycerols, triglycerols, tetraglycerols, and higher oligomeric glycerol polyethers.

Preparation of Polyglycerols

The invention includes a process for preparing polyglycerols by reacting glycerol, polyglycerol, or a mixture thereof in the presence of a calcium containing compound to form a solution containing polyglycerol. The glycerol, polyglycerol, or mixture thereof and calcium containing compound are preferably mixed well. Suitable starting polyglycerols include, but are not limited to, diglycerols, triglycerols, tetraglycerols, higher oligomeric glycerol polyethers, and mixtures thereof. Furthermore, reclaimed glycerol obtained by distilling the excess glycerol from a previously prepared polyglycerol can be used as a starting material. Preferably, most, if not all, ions (except for calcium) and ion containing complexes, such as sodium, potassium, magnesium, and ion containing clays, such as zeolite, diatomaceous, and earth, are removed from the reclaimed glycerol prior to its reaction with the calcium containing compound.

The reaction is typically performed at the same process conditions as polymerization with other alkali metals, such as sodium. Generally, the reaction is performed at a temperature of from about 200 to about 240° C. and preferably at from about 220 to about 240° C. According to a preferred embodiment, the reaction is performed at about 230° C. The reaction is broadly performed at a pressure of from about 10 to about 400 mm Hg and preferably from about 100 to about 200 mm Hg. According to a preferred embodiment, the reaction is performed at a pressure of about 150 mm Hg.

In general, the presence of water in the reaction mixture slows down the reaction. Therefore, it is preferable to have little, if any, water present in the reaction mixture during polymerization. The reaction mixture preferably contains less than about 0.5% and more preferably contains less than about 0.2% by weight of water, based upon 100% total weight of reaction mixture. According to a preferred embodiment, a solvent that promotes water removal, such as toluene, is added to the reaction mixture. According to another preferred embodiment, a heavy inert gas, e.g., nitrogen is sparged through the mixture during the reaction.

Generally, the glycerol, polyglycerol, or mixture thereof is reacted with a catalyzing effective amount of the calcium containing compound. The molar ratio of glycerol, polyglycerol, or mixture thereof to calcium containing compound broadly ranges from about 1:0.0002 to about 1:0.005, preferably from about 1:0.0005 to about 1:0.005, and more preferably from about 1:0.001 to about 1:0.002.

When the calcium containing compound is calcium hydroxide, the weight ratio of glycerol, polyglycerol, or mixture thereof to calcium hydroxide preferably ranges from about 1:0.0003 to about 1:0.009, more preferably ranges from about 1:0.0009 to about 1:0.009, and most preferably ranges from about 1:0.002 to about 1:0.004.

Generally, the reaction mixture is substantially free of alkali (group I) metals, such as sodium and potassium. The reaction mixture preferably contains less than about 0.05% and more preferably less than about 0.0005% by weight of alkali (group I) metals, based upon 100% total weight of reaction mixture.

The reaction mixture can be monitored to assess the completion of the reaction, by, for example, gas chromatography and any method of determining hydroxyl value known in the art.

The resulting solution contains polyglycerol and glycerol. The glycerol can be removed by any method known in the art, such as vacuum distillation or steam stripping. The solution preferably contains less than about 8% and more preferably less than about 5% by weight of cyclic polyglycerols, based on 100% weight of total polyglycerols in the solution.

Preparation of Polyglycerol Esters

According to the present invention, a polyglycerol ester is prepared by esterifying polyglcerol with one or more fatty acids or transesterifying polyglycerol with one or more monoglycerides, diglycerides, or triglycerides in the presence of a calcium containing compound. The polyglycerol may be prepared by the method described above or by any other method known in the art.

Suitable fatty acids include, but are not limited to, saturated and unsaturated, linear and branched $C_6$ to $C_{22}$ fatty acids. Non-limiting examples of suitable saturated fatty acids include lauric acid, stearic acid, isostearic acid, oleic acid, palmitic acid, behenic acid, myristic acid, caprylic acid, capric acid, caproic acid, arachidic acid, and mixtures thereof. Non-limiting examples of suitable unsaturated fatty acids include myristoleic acid, linoleic acid, oleic acid, licaneic acid, ricinoleic acid, eleostearic acid, and erucic acid. Triglycerides that contain any of these fatty acids are also suitable.

Esterification may be performed at the same process conditions as esterification with other alkali bases, such as sodium hydroxide, sodium carbonate, and sodium acetate. Examples of such process conditions include, but are not limited to, those described in U.S. Pat. Nos. 5,585,506, 4,517,360, 5,006,648, 5,071,975, 5,079,355, and 3,963,699.

According to a preferred embodiment, the esterification (or transesterification) is performed by heating the polyglycerol and fatty acid or triglyceride in the presence of the calcium containing compound. The esterification is generally performed at a temperature of from about 160° to about 260° C. and preferably performed at from about 210 to about 250° C. According to a preferred embodiment, the esterification is performed at a temperature of about 230° C. The reaction mixture is typically maintained at a pressure of from about 10 to about 760 mm Hg and preferably is maintained at a pressure of from about 150 to about 760 mm Hg. Transesterification takes place under the same conditions with the exception that the preferred reaction temperature is 230° to 260° C.

The molar ratio of polyglycerol to fatty acid equivalent (or triglyceride) in the reaction mixture broadly ranges from about 1:0.5 to about 1:10. The molar ratio can be varied in order to vary the performance of the polyglycerol ester produced. Generally, the higher the molar ratio of polyglyercol to fatty acid (or triglyceride), the lower the hydrophilic-lipophilic balance (HLB) of the product.

Typically, a catalyzing effective amount of the calcium containing compound is present in the reaction mixture. The molar ratio of polyglycerol to calcium containing compound in the reaction mixture generally ranges from about 1:0.2 to about 1:0.0002, preferably from about 1:0.04 to about 1:0.0008, and more preferably from about 1:0.004 to about 1:0.001.

According to one preferred embodiment, calcium hydroxide is used as the catalyst at a concentration of about from 0.01 to about 5% by weight, based on 100% total weight of the reaction mixture. More preferably, the concentration of calcium hydroxide in the reaction mixture ranges from about 0.01 to about 2% by weight, based on 100% total weight of the reaction mixture. Since the concentration of calcium hydroxide is relatively low, the calcium may be easily filtered out of the mixture and is not likely to precipitate out of the mixture.

Generally, the reaction is performed for about 1 to about 10 hours and preferably for about 2 to about 4 hours. More preferably, the reaction is continued until the reaction mixture is clear and has an Acid Value as measured by American Oil Chemists Society (A.O.C.S.) Official Method Te 1a-64 of less than 2.

Once the reaction is complete, the reaction mixture can be neutralized by any method known in the art, such as with a neutralizing agent. Suitable neutralizing agents include, but are not limited to, phosphoric acid, phosphorous acid, lactic acid, acetic acid, hydrochloric acid and citric acid.

Generally, the reaction mixture is substantially free of alkali (group I) metals, such as sodium and potassium. The reaction mixture preferably contains less than about 0.02% and more preferably less than about 0.0001% by weight of alkali (group I) metals, based upon 100% total weight of reaction mixture.

The resulting solution preferably contains less than about 8% and more preferably less than about 5% by weight of cyclic polyglycerol esters, based on 100% weight of total polyglycerol esters in the solution.

The following examples are intended to describe the present invention without limitation.

Procedure for Determining Polyglycerol Distribution in Mixture Containing Polyglycerols In the examples below, the distribution of polyglycerols in a solution was determined according to the following procedure. A 10–50 mg sample of polyglycerol was derivatized with 5 ml of silylating reagent (hexamethyldisilazane (HMDS): trimethylchlorosilane (TMCS): pyridine, 3:1:9 from Supelco, Inc. of Bellefonte, Pa.) following Supelco's recommended procedure. Supelco's recommended procedure is as follows:

1. Weigh 1–10 mg of sample into a 5 ml reaction vessel. If appropriate, dissolve the sample in an appropriate solvent. If sample is in aqueous solution, evaporate to dryness, then use neat or add solvent;
2. Add excess silylating reagent at full strength or with a solvent; and
3. Allow the mixture to stand until silylation is complete. To determine when derivation is complete, analyze aliquots of the sample at selected time intervals until no further increase in product peak(s) is observed.

The polyglycerol distribution was determined by gas chromatography using a DB-5HT capillary column (30 m×0.32 mm ID×0.1 µm film thickness), available from J & W Scientific Inc. of Folsom, Calif., and an HP Series 5890 Chromatography equipped with an FID detector. The conditions for the column were as follows: helium carrier gas (2 ml/min); column head pressure (6.9 psig); injector temperature (375° C.); detector temperature (375° C.); temperature program (100–375° C. at 10° C./min ramp, 5 min at 100° C. and 10 min at 375° C.); and a 3 µl injection volume. Identification of the eluting compounds was determined by gas chromatography and mass spectroscopy.

Procedure for Determining Polyglycerol Distribution in a Mixture Containing Polyglycerol Esters A 2 g sample of polyglycerol ester and 50 ml of 0.8 N ethanolic potassium hydroxide were placed into a 250 ml Erlenmeyer flask and refluxed for 1 hour. While still warm, the solution was neutralized to a Congo red end point with hydrochloric acid. The fatty acid was allowed to settle and approximately 10 ml of the ethanol layer (which contained free polyglycerol) was removed and transferred to a 20 ml scintillation vial, followed by the addition of approximately 10 ml of an aqueous saturated sodium chloride solution. The mixture in the vial was then boiled to remove residual ethanol. The vial was cooled and 3 ml of the solution was removed and filtered through a disposable HPLC filter into a clean 20 ml scintillation vial. Approximately 5 ml of isopropyl alcohol was added to the vial and the resulting mixture was evaporated to dryness. The dried sample, which contained polyglycerol, was then analyzed by the method described above for determining the polyglycerol distribution in a mixture.

Procedure for Determining Acid Value

The acid value of the reaction mixture was determined according to the American Oil Chemists Society (A.O.C.S.) Official Method Te 1a-64.

Procedure for Determining Hydroxyl Value

The hydroxyl value of the reaction mixture was determined according to A.O.C.S. Official Method Cd 13-60.

Procedure for Determining Saponification Value

The saponification value of the reaction mixture was determined according to A.O.C.S. Official Method Cd 3-25.

EXAMPLE 1

Calcium Hydroxide Catalyzed Preparation of Polyglycerol

Into a clean 100 gallon stainless steel reactor was charged 800 lbs. (3944 moles) of glycerol and 0.8 lbs. (0.0108 moles) of calcium hydroxide. The reactor was equipped with a variable speed agitator, nitrogen sparge, steam sparge, vacuum capabilities to below 1 mm Hg, a packed column and reflex splitter, temperature and vacuum control capabilities, internal cooling coils, heating jacket, and a 30 gallon receiver.

A vacuum of 200 mm Hg was applied to the reactor and the glycerol-calcium hydroxide mixture was agitated and heated to 230° C. Thereafter, the vacuum was reduced gradually to 150 mm Hg and the reflux ratio varied from 1:1 to 10:1 over a 15 hour period at such a rate as to maintain a column head temperature below 90° C. The reaction was monitored by Hydroxyl Value and considered complete when a Hydroxyl Value of 1480 was achieved. The consumption of glycerol and the growth of linear polyglycerols and cyclic polyglycerols was monitored by gas chromatography. At completion, the reaction mixture contained 43% by weight of glycerol, 33% by weight of diglycerol, 14% by weight of triglycerol, 5% by weight of tetraglycerol, 2% by weight of pentaglycerol, and 2.3% by weight of cyclic polyglycerol.

Upon reaching the Hydroxyl Value of 1480, the reaction mixture was cooled to 200° C. and the reactor was configured for glycerol stripping and steam stripping. The bulk of the glycerol was stripped by applying a vacuum of 4 mm Hg to the reactor while heating at 200° C. The remainder of glycerol was stripped by introducing steam into the bottom valve of the reactor. A total of 338 lbs. of glycerol and 396 lbs. of polyglycerol were recovered. The composition contained 0.12% by weight of glycerol, 42% by weight of diglycerol, 23% by weight of triglycerol, 14% by weight of tetraglycerol, 10% by weight of pentaglycerol, 6% by weight of hexaglycerol, and 4.5% by weight of cyclic polyglycerol, based upon 100% total weight of polyglycerol.

COMPARATIVE EXAMPLE 1

Potassium Hydroxide Catalyzed Preparation of Polyglycerol

Into a clean 5 L round bottom flask was charged 3.9 kg. (42.3 moles) of glycerol and 49 g. (46% aqueous, 0.31 moles) of potassium hydroxide. The flask was equipped with a variable speed agitator, nitrogen sparge, steam sparge, vacuum capabilities down to 1 mm Hg, a packed column, temperature and vacuum control capabilities, and a 1 L receiver.

A vacuum of 200 mm Hg was applied to the reactor and the glycerol-calcium hydroxide mixture was agitated and heated to 230° C. Thereafter, the vacuum was reduced gradually to 150 mm Hg and the reflux ratio varied from 1:1 to 10:1 over a 15 hour period at such a rate as to maintain a column head temperature below 90° C. The reaction was monitored by Hydroxyl Value and Gas Chromatography as described in Example 1 and considered complete when a Hydroxyl Value of 1435 was achieved.

Upon reaching the Hydroxyl Value of 1435, the reaction mixture was cooled to 200° C. and the reactor was configured for glycerol stripping and steam stripping. The bulk of the glycerol was stripped by applying a vacuum of 4 mm Hg to the reactor while heating at 200° C. The remainder of glycerol was stripped by introducing steam into the bottom valve of the reactor. The final composition contained 0.84% by weight of glycerol, 47% by weight of diglycerol, 32% by weight of triglycerol, 11% by weight of tetraglycerol, 5% by weight of pentaglycerol, 2% by weight of hexaglycerol, and 2% by weight of cyclic polyglycerol, based upon 100% total weight of polyglycerol.

EXAMPLE 2

Preparation of Polyglycerol Ester from Polyglycerol with Calcium Hydroxide Catalyst Into a 2 L round bottom flask was placed 612 g (2.35 moles) palmitic acid and 588 g (2.35 moles) polyglycerol prepared by the calcium hydroxide catalyzed method of Example 1. The polyglycerol used contained 4.5% cyclic polyglycerol. The flask was fitted with a mechanical stirrer, temperature control, and nitrogen sparge. The mixture was heated to 230° C. for 2 hours, until it was clear and had an Acid Value below 2. The calcium hydroxide, remaining from the polyglycerol forming process, was neutralized by adding 0.6 g of an phosphoric acid aqueous solution (85% phosphoric acid and 15% water) while the mixture was heated at 230° C. The mixture was stirred for another 15 minutes and then cooled. The mixture was filtered through Perlite available from Harborlite Corp., of Superior, Ariz., and analyzed. The mixture had the following characteristics: Acid Value of 0.5; Hydroxyl Value 462, compared to a theoretical Hydroxyl Value of 467; Saponification Value 115, compared to theoretical Saponification Value of 114; Gardner color 1+; clear appearance at melt; 4.2% cyclic polyglycerols; mild odor; and bland taste.

This procedure was repeated with lauric acid, oleic acid, and stearic acid. The resulting concentrations of cyclic polyglycerols in the esters formed with these fatty acids were 5.4%, 4.7%, and 5.8%, respectively.

EXAMPLE 3

Preparation of Polyglycerol Ester from Polyglycerol and a Triglyceride with Calcium Hydroxide Catalyst Into a 12 L round bottom flask was placed 4,940 g (5.64 moles) sunflower oil and 4,086 g (17.39 moles) polyglycerol prepared by the calcium hydroxide catalyzed method of Example 1. The flask was fitted with a mechanical stirrer, temperature control, and nitrogen sparge. The polyglycerol contained 2% by weight of cyclic polyglycerols, based upon 100% total weight of polyglycerols. The mixture was heated to 255° C. for 4 hours, until it was clear. The calcium hydroxide remaining from the polyglycerol forming process was neutralized by adding 13 g of a phosphoric acid aqueous solution (85% phosphoric acid and 15% water) at 255° C. The mixture was stirred for another 15 minutes, sampled for Neutralization Value, which was found to be <0.1 and then cooled. The mixture was filtered through Perlite available from Harborlite Corp., of Superior, Ariz., and analyzed. The mixture had the following characteristics: acid value 1.9, hydroxyl value 479, saponification value 112, Gardner color 4, 5.9% cyclic polyglycerols, mild odor and bland taste.

COMPARATIVE EXAMPLE 2

Preparation of Polyglycerol Ester from Polyglycerol and Palmitic Acid with Potassium Hydroxide Catalyst Into a 2 L round bottom flask was placed 712 g (2.74 moles) palmitic acid and 488 g (2.11 moles) polyglycerol prepared by the potassium hydroxide catalyzed method of Example 2. The flask was fitted with a mechanical stirrer, temperature control, and nitrogen sparge. The polyglycerol contained 2% by weight of cyclic polyglycerols, based upon 100% total weight of polyglycerols.

The mixture was heated to 230° C. for 3–4 hours, until it was clear and had an Acid Value below 2. The potassium hydroxide remaining from the polyglycerol forming process was neutralized by adding 8.9 g of a phosphoric acid aqueous solution (85% phosphoric acid and 15% water) at 230° C. The mixture was stirred for another 15 minutes and then cooled. The mixture was filtered through Perlite available from Harborlite Corp., of Superior, Ariz., and analyzed. The mixture had the following characteristics: Acid Value of 0.3; Hydroxyl Value 319, compared to a theoretical Hydroxyl Value of 398; Saponification Value 133, compared to theoretical Saponification Value of 133; Gardner color 6+; clear appearance at melt; 15.2% cyclic polyglycerols; mild odor; and bland taste.

COMPARATIVE EXAMPLE 3

A polyglycerol ester of lauric acid, available as glycerol monolaurate from Coleman Chemical Co. of Joliet, Ill., was analyzed and found to contain 9.9% by weight of cyclic polyglycerol ester, based upon 100% total weight of polyglycerol ester.

A polyglycerol ester of oleic acid, available as decaglycerol tetraoleate from George A. Goulston Co. of Monroe, N.C., was analyzed and found to contain 9.6% by weight of cyclic polyglycerol ester, based upon 100% total weight of polyglycerol ester.

All patents, publications, applications, and test methods mentioned above are hereby incorporated by reference. Many variations of the present matter will suggest themselves to those skilled in the art in light of the above detailed description. All such obvious variations are within the patented scope of the appended claims.

What is claimed is:

1. A method of preparing a solution comprising polyglycerol comprising the step of polymerizing glycerol, polyglycerol, or a mixture thereof in the presence of a calcium containing compound.

2. The method of claim 1, wherein the calcium containing compound is selected from calcium hydroxide, calcium oxide, calcium carbonate, and any combination of any of the foregoing.

3. The method of claim 2, wherein the calcium containing compound is calcium hydroxide.

4. The method of claim 1, wherein the molar ratio of glycerol, polyglycerol, or mixture thereof to calcium containing compound ranges from about 1:0.0002 to about 1:0.005.

5. The method of claim 4, wherein the molar ratio of glycerol, polyglycerol, or mixture thereof to calcium containing compound ranges from about 1:0.0005 to about 1:0.005.

6. The method of claim 3, wherein a catalyzing effective amount of calcium hydroxide is reacted with the glycerol, polyglycerol, or mixture thereof.

7. The method of claim 3, wherein the weight ratio of glycerol, polyglycerol, or mixture thereof to calcium hydroxide ranges from about 1:0.009 to about 1:0.0003.

8. The method of claim 7, wherein the weight ratio of glycerol, polyglycerol, or mixture thereof to calcium hydroxide ranges from about 1:0.009 to about 1:0.0009.

9. The method of claim 1, wherein the polymerization is performed at a temperature of from about 200 to about 240° C.

10. The method of claim 9, wherein the polymerization is performed at a temperature of from about 220 to about 240° C.

11. The method of claim 10, wherein the polymerization is performed at a temperature of about 230° C.

12. The method of claim 1, wherein the polymerization is performed at a pressure of from about 10 to about 400 mm Hg.

13. The method of claim 12, wherein the polymerization is performed at a pressure of from about 100 to about 200 mm Hg.

14. The method of claim 13, wherein the polymerization is performed at a pressure of about 150 mm Hg.

15. The method of claim 1, further comprising the step of purifying the solution containing the polyglycerol after polymerization.

16. The method of claim 1, further comprising the step of removing glycerol from the solution containing the polyglycerol.

17. The method of claim 16, wherein the removal step comprises vacuum distilling or steam stripping glycerol from the solution containing the polyglycerol.

18. The method of claim 1, wherein the solution comprises less than about 8% by weight of cyclic polyglycerols, based upon 100% by weight of polyglycerols.

19. The method of claim 18, wherein the solution comprises less than about 5% by weight of cyclic polyglycerols, based upon 100% by weight of polyglycerols.

20. A method of preparing a solution containing polyglycerols wherein the solution contains less than about 5% by weight of cyclic polyglycerols, based upon 100% by weight of total polyglycerols, the method comprising the step of reacting glycerol with a calcium containing compound in solution to form the solution containing polyglycerols.

21. A method of preparing a polyglycerol ester comprising the step of esterifying a polyglycerol with a fatty acid or triglyceride in the presence of a calcium containing compound.

22. The method of claim 21, wherein the calcium containing compound is selected from calcium hydroxide, calcium oxide, calcium carbonate, and any combination of any of the foregoing.

23. The method of claim 22, wherein the calcium containing compound is calcium hydroxide.

24. The method of claim 23, wherein a catalyzing effective amount of calcium hydroxide is present during the reaction.

25. The method of claim 21, wherein the molar ratio of polyglycerol to calcium containing compound ranges from about 1:0.2 to about 1:0.0002.

26. The method of claim 25, wherein the molar ratio of polyglycerol to calcium containing compound ranges from about 1:0.04 to about 1:0.0008.

27. The method of claim 23, wherein the concentration of calcium hydroxide in the reaction mixture is about from 0.01 to about 5% by weight, based upon 100% total weight of the reaction mixture.

28. The method of claim 27, wherein the concentration of calcium hydroxide in the reaction mixture ranges from about 0.01 to about 2% by weight, based upon 100% total weight of the reaction mixture.

29. The method of claim 21, wherein the fatty acid is selected from the group consisting of lauric acid, stearic acid, isostearic acid, oleic acid, palmitic acid, behenic acid, myristic acid, caprylic acid, capric acid, caproic acid, arachidic acid, myristoleic acid, linoleic acid, oleic acid, licaneic acid, ricinoleic acid, eleostearic acid, erucic acid, and any combination of any of the foregoing.

30. The method of claim 21, wherein the molar ratio of polyglycerol to fatty acid ranges from about 1:0.5 to about 1:10.

31. The method of claim 21, wherein the etherification step is performed at a temperature of from about 160 to about 260° C.

32. The method of claim 31, wherein the etherification step is performed at a temperature of from about 210 to about 250° C.

33. The method of claim 32, wherein the etherification step is performed at a temperature of about 230° C.

34. The method of claim 21, wherein the esterification step is performed for from about 1 to about 10 hours.

35. The method of claim 34, wherein the esterification step is performed for from about 2 to about 4 hours.

36. The method of claim 21, wherein the polyglycerol ester is prepared in solution.

37. The method of claim 36, further comprising purifying the solution comprising the polyglycerol ester.

38. The method of claim 36, wherein the solution comprises less than about 8% by weight of cyclic polyglycerol esters, based upon 100% by weight of polyglycerol esters.

39. The method of claim 38, wherein the solution comprises less than about 5% by weight of cyclic polyglycerol esters, based upon 100% by weight of polyglycerol esters.

* * * * *